US00PP15702P2

(12) United States Plant Patent
Pounders, Jr.

(10) Patent No.: US PP15,702 P2
(45) Date of Patent: Mar. 29, 2005

(54) ***ILEX* HYBRID VARIETY NAMED XIA YEN**

(50) Latin Name: *Ilex×attenuata*
Varietal Denomination: Xia Yen

(75) Inventor: Cecil T. Pounders, Jr., 3140 Old Moulton Rd., SW., Decatur, AL (US) 35603

(73) Assignee: Cecil T. Pounders, Jr., Biloxi, MS (US)

( * ) Notice: Subject to any disclaimer, the term of this patent is extended or adjusted under 35 U.S.C. 154(b) by 0 days.

(21) Appl. No.: 09/468,889

(22) Filed: Dec. 22, 1999

(51) Int. Cl.[7] ..... A01H 5/00
(52) U.S. Cl. ..... Plt./247

(58) Field of Search ..... Plt./247

(56) References Cited

U.S. PATENT DOCUMENTS

PP11,741 P2 * 1/2001 Pounders, Jr. ..... Plt./247

* cited by examiner

*Primary Examiner*—Kent Bell

(57) ABSTRACT

Xia Yen is a distinctive new evergreen holly distinguished from all other forms of *Ilex* known to me in that it combines a unique combination of desirable landscape and production traits from *Ilex opaca* and *Ilex cassine*. Plants have distinctive lustrous leaves, produce an erect narrow symmetrical crown without extensive shearing, and have the environmental tolerances of the *Ilex opaca* parent. Xia Yen is being marketed bearing the Dixie Star Holly trademark.

2 Drawing Sheets

SUMMARY OF THE INVENTION

My invention is a unique ornamental type of *Ilex* selected by me from a second generation group of open-pollinated seedlings of *Ilex×attenuata* (*I. opaca×I. cassine*).

My goal was to select a tough ornate shrub combining *I. cassine's* fine leaf texture and uniform branching with *I. opaca's* better leaf color and tolerance of cold and moisture stress. This invention incorporates the desired traits from the original species differentiating it from all other forms of *Ilex* of which I am aware. The new clone has been named the Xia Yen variety.

The variety exhibits the following combination of traits:

(a) lustrous evergreen leaves intermediate in texture between leaves of the two parental species, (b) balanced, vigorous pyramidal crown without extensive shearing due to strong apical dominance, (c) annual crops of bright red fruit in early fall which remain until spring, (d) environmental tolerances equivalent to *I. opaca*.

Xia Yen was selected as a superior replacement for *Ilex×attenuata* 'Foster #2' (unpatented), a holly selection extensively planted in the southern United States. Under production conditions Xia Yen is self-branching with strong apical dominance which reduces production cost when compared to Foster holly while in landscapes Xia Yen displays superior leaf color and more symmetric branching. Xia Yen resembles Foster #2 Holly's leaf texture and crown shape more than Xia Xiang (U.S. Plant Pat. No. 10,526) and Huo Yen (U.S. Plant Pat. No. 11,741) Hollies do.

My new variety, Xia Yen, has been asexually propagated by soft-wood cuttings at Mobile, Decatur and Loxley, Ala. Propagules demonstrated that the distinctive combination of characteristics are fixed and reproduce true to type to successive generations.

Xia Yen is being marketed bearing the Dixie Star Holly trademark.

BRIEF DESCRIPTION OF THE PHOTOGRAPHS

The accompanying photographs show typical plants of my new variety of *Ilex* during fall and early winter as depicted in color as true as is reasonably possible to make the same in color photographs of the character. The specimens illustrated were being grown in the ground at Decatur, Ala. and in nursery containers at Loxley, Ala.

DETAILED DESCRIPTION

Figure 1:
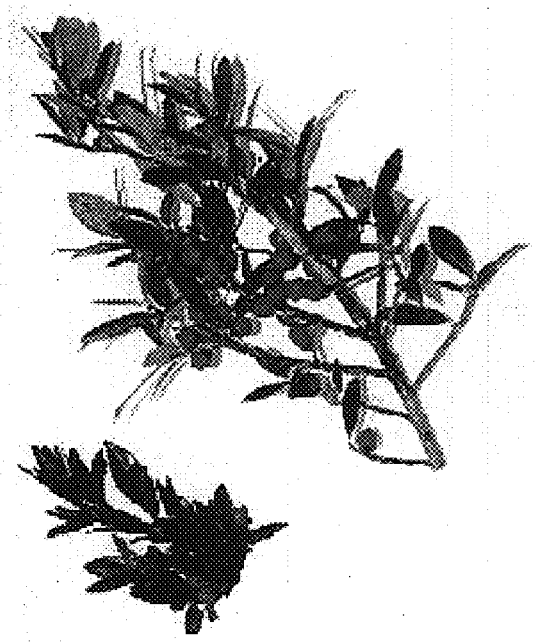
FIG. 1 illustrates shape, size and color of fruit and foliage.
Figure 2:
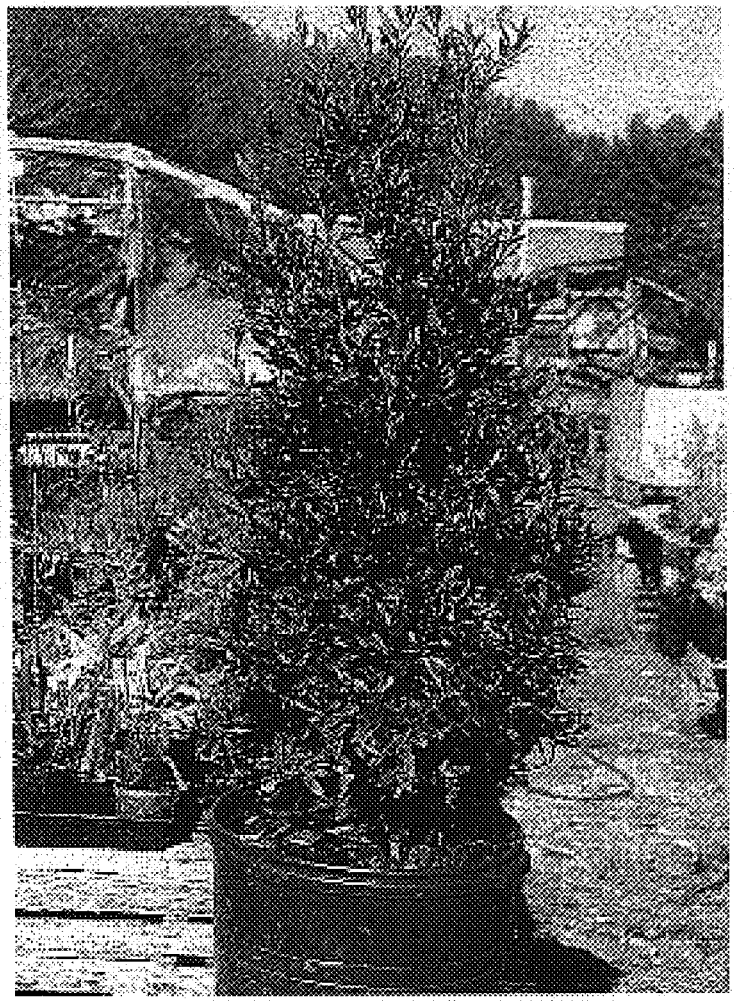
FIG. 2 illustrates plant uniformity under nursery conditions.

The following is a detailed description of my new variety of *Ilex* made from observation of 7 year old plants growing in the ground at Baldwin County, Ala. Color terminology is in accordance with The R.H.S. Colour Chart of The Royal Horticultural Society, London, England.

Class *Ilex×attenuata*.
Parentage: Unknown.
Foliage:

*Type*.—Evergreen, glossy, coriaceous. Leaves elliptic — lanceolate, serrate with minute spine-tipped teeth; Bases narrowly tapered, apices acute.

*Size*.—leaf size is affected by environmental factors such as light intensity and plant nutrition. Leaf size ranges from 4–6 cm long and 1–2 cm wide.

*Petiole*.—Ranges from 7 to 9 mm in length, grooved, color Greyed Red Group 178B.

*Color*.—Upper surfaces of mature leaves are closest to Green Group 137A; lower surface Green Group 138B.

Stems:

*Size*.—Stem length, width and internode length are under strong environmental control, increasing with favorable fertility and moisture or decreased light. Stem measurements taken in the outer canopy of the plant used for description, reflecting growth of the previous two seasons, had lengths ranging from 6 to 17 cm, caliper ranging from 2 mm at tips to 8 mm at the base and internodes of 1.5 to 4 cm.

*Color.*—On new growth stems are Greyed Purple 187A, maturing to Greyed Green Group 197A. Bark on trunks and branches is Black Group 202D.

Inflorescence and Fruit:

*Flowers.*—Pistillate, usually solitary in leaf axils or at nodes just below leaves on initial spring growth; sepals 4, petals 4; colored Orange White Group 159D on both surfaces. All other floral morphology such as petal and sepal shape, length, width and margins has been observed to be typical of *Ilex*× *attenuata*.

*Fruit.*—Drupe containing 4 woody pyrenes; ellipsoid; approximately 8 to 11 mm in diameter.

*Fruit color.*—Dull to semi-glossy, Red Group 46B.

Plant growth characteristics: Plants have a slender conical growth habit with seven-year individuals growing to roughly 3 m in height and 1 m in width. Without pruning, growth slows but continues proportionally with 15 year individuals generally in the range of 4 to 6 m in height, 1.5 to 2.5 m in width, and main trunk diameter of 4 to 8 cm depending on growing conditions such as moisture, soil fertility and light intensity to which 'Xia Yen' is exposed during growth. Branching is symmetrical without extensive pruning with plants establishing a dominant central trunk. Xia Yen produces adequate annual crops of colorful red berries but does not fruit as heavily as Huo Yen holly. This variety's merit is a unique combination of lustrous dark green leaves and red fruit in combination with superior plant form.

Environmental tolerance: Testing to date indicates that Xia Yen successfully combines textural qualities of *Ilex cassine* with the environmental adaptions of *Ilex opaca*. This new variety is adapted to the same landscape conditions and climatic range associated with *I. opaca*. Parental species have the same pest problems thus no improved pest tolerance has been observed.

I claim:

1. A new and distinct variety of *Ilex*×*attenuata* plant named 'Xia Yen', as illustrated and described particularly as to the unique combination of:

(a) annual abundant crops of fruit maturing to vibrant red in early fall then persisting until spring, (b) evergreen, fine textured leaves which retain lustrous green coloration even when plant is heavily berried, (c) produces an erect narrow symmetrical pyramidal crown without extensive shearing, (d) environmental tolerance equivalent to *I. opaca*.

* * * * *